(12) United States Patent
Choudhary (10) Patent No.: US 6,689,107 B1
(45) Date of Patent: Feb. 10, 2004

(54) NEEDLE ASSEMBLY

(76) Inventor: Prajenda Pandurang Choudhary, 3 Spode Grove Wesbury Park, Newcastle under Lyme, Staffordshire ST5 4HF (GB)

( * ) Notice: Subject to any disclaimer, the term of this patent is extended or adjusted under 35 U.S.C. 154(b) by 0 days.

(21) Appl. No.: 09/830,911

(22) PCT Filed: Nov. 4, 1999

(86) PCT No.: PCT/GB99/03644

§ 371 (c)(1),
(2), (4) Date: May 1, 2001

(87) PCT Pub. No.: WO00/25845

PCT Pub. Date: May 11, 2000

(30) Foreign Application Priority Data

Nov. 4, 1998 (GB) .............................. 9824000
Feb. 23, 1999 (GB) .............................. 9903974

(51) Int. Cl.7 .............................................. A61M 5/00
(52) U.S. Cl. ....................................... 604/192; 604/110
(58) Field of Search ................................. 604/110, 181, 604/192, 198, 197

(56) References Cited

U.S. PATENT DOCUMENTS

| 5,360,211 A | 11/1994 | Smith et al. |
| 5,630,803 A | 5/1997 | Tamaro |
| 5,795,336 A | 8/1998 | Romano et al. |

FOREIGN PATENT DOCUMENTS

| EP | 0 413 872 | 2/1991 |
| EP | 0 555 974 | 8/1993 |
| EP | 0 743 073 | 11/1996 |
| EP | 0 750 916 | 1/1997 |
| GB | 754 447 | 8/1956 |
| WO | 94/09840 | 5/1994 |

*Primary Examiner*—Manuel Mendez
(74) *Attorney, Agent, or Firm*—Smith-Hill and Bedell (57) ABSTRACT

A needle assembly (10) comprising a needle (16) of elliptical cross section which extends through a cylindrical housing. A movable member (26) through which the needle (16) passes slidably locates within the housing and comprises a cylindrical tube (38) extending from the housing, with an elliptical opening (42) at the free end thereof. The needle (16) can only extend from the member (26) through the opening (42) when the housing member (26) is rotated into elliptical alignment with the needle and slid into the housing.

19 Claims, 4 Drawing Sheets

NEEDLE ASSEMBLY

This invention concerns a needle assembly, particularly but not exclusively a needle assembly for use with syringes, drips, vacutainers or other instruments which include a needle for administering a substance to a body or taking a sample therefrom; and also instruments including such an assembly.

Needles are used extensively in medicine, veterinary science and elsewhere for providing injections, drips and the like. Needles can be used when taking samples and also administering substances by injection or a drip. Medical staff and others can often injure themselves on needles. When dealing with infected persons or animals this can produce a considerable risk of infection to the user. Accidents can also occur where discarded needles are found, and particularly by children. When such needles have been used by persons administering illegal drugs the risk of a serious infection is increased.

The term "needle instrument" as hereinafter used in this specification is to be understood as covering any instrument which requires a needle or other elongate projection for inserting into a body, which may be usable for instance for administering a substance to a body or taking a sample therefrom, or puncturing the skin. The needle/projection may be hollow or solid. Examples of such instruments are indicated above.

According to the present invention there is provided a needle assembly, the assembly comprising a needle and a housing in which the needle is located and from which the needle can selectively extend, the assembly being arranged such that the needle can only extend from the housing when in a particular alignment relative to the housing.

The needle may have a non-circular cross-section for at least part of its length, and the housing may have a restrictive part with a non-circular cross-section through which the needle can only extend when in a particular alignment relative thereto.

The housing preferably comprises a first part rigidly fixed relative to the needle and a second part movable relative to the needle, the second part being movable when the needle is in the particular alignment to a use position wherein the needle extends from the housing. The second part preferably includes the restrictive part.

The first part is preferably in the form of a receptacle which movably locates a portion of the second part and from which a further portion of the second part extends, with a greater portion of the second part being located in the first part when in the use position.

A component of the second part is preferably slidably movable within the first part. The needle preferably extends through the first part. A free end of the second part may have a roughened surface to be non-rotatably engageable in use against a person's skin.

The second part is preferably spring urged away from the use position and/or the particular relative alignment with the needle. The second part is desirably spring urged away from the use position and the particular relative alignment, and desirably by a single spring, which spring may comprise a helical spring which may extend around the needle, and is desirably substantially co-axial therewith.

First means are preferably provided for selectively retaining the needle and second part in said particular alignment when the needle is located wholly within the housing.

Second means are preferably provided for selectively retaining the needle and second part in said particular alignment when the needle extends from the housing.

The first retaining means may comprise one or more projections on a one of the first or second parts which is selectively locatable in a corresponding recess or recesses in the other of the first or second parts.

Alternatively, the first retaining means may comprise a projection on the second part which is engageable against an abutment on the first part when in the particular alignment, and the projection and abutment desirably have sufficient depth for engagement to continue as the needle is moved to extend from the housing, and desirably until the second retaining means becomes operative.

The second retaining means may comprise an elongate projection on a one of the first or second parts which is selectively slidably locatable in a corresponding recess in the other of the first or second parts. Alternatively the second retaining means may comprise an elongate recess on a one of the first or second parts which selectively slidably locates a corresponding projection on the other of the first or second parts. The elongate projection or recess is preferably provided on the first part.

In alternative embodiments guide means may be provided which only permit the second part to move into the first part when in said particular alignment. Said guide means may comprise an elongate projection on the first part which only permits movement when engaging in a recess in the second part. The recess preferably extends for the whole length of the second part.

A plurality of recesses are preferably provided, with some of the recesses being blind by only extending for a part of the length of the second part. The blind recesses are preferably of a length such that when the elongate projection reaches the closed end thereof, the needle has not yet started to extend from the housing.

As an alternative to an elongate projection, a slidable projection may be provided.

Means may be included to provide a visual indication when the needle is in the particular relative alignment, and said means may comprise alignable markings on the first and second parts.

The first part may comprise a cylinder and said component of the second part preferably comprises a member which slidingly fits in the cylinder.

The restrictive part of the housing may be provided substantially at the end of the second part of the housing furthest from the first part thereof.

The restrictive part and/or the needle may have a substantially oval or elliptical cross-section, and desirably both are substantially oval or elliptical with the needle only slidingly fitting through the restrictive part when in a substantially parallel alignment thereto.

Alternatively the restrictive part and/or the needle may have a polygonal cross-section. Desirably the restrictive part and/or needle are of a triangular cross-section, and desirably both have a triangular cross-section with the needle only slidingly fitting through the restrictive part when in a substantially parallel alignment thereto.

The second part between said component and the restrictive part may comprise a tube through which the needle is movable, and the tube preferably has a circular cross-section.

The first part preferably rigidly mounts the proximal end of the needle.

In an alternative embodiment the housing between the first and second parts comprises a variable length portion such that the housing can reduce in length to permit the needle to extend therefrom.

The housing may comprise a third part located between the first and second parts, and a variable length portion is desirably provided between the first and third parts. A variable length portion may also be provided between the second and third parts.

Third means are preferably provided for selectively retaining the needle and the second part in said particular alignment.

The third retaining means may comprise one or more projections engageable in a corresponding recess or recesses, which recess or recesses are non-rotatably arranged relative to the needle. Alternatively, the third retaining means may comprise one or more recesses in which a corresponding projection or projections are engageable, which projection or projections are non-rotatably arranged relative to the needle.

The corresponding recess or recesses; or corresponding projection or projections of the third retaining means, are desirably provided on the third part.

The visual indication means may comprise alignable markings on any of the first, second and third parts.

The second part preferably comprises a portion proximal of the restrictive part which accepts the needle in any orientation, and desirably receives the distal end of the needle when the assembly is in a rest condition.

The or each variable length portion of the housing preferably comprises a flexible cover around the needle, and the cover is preferably substantially inelastic. The or each variable length portion preferably comprises a spring urging said portion to its maximum length. The springs preferably extend substantially co-axially around the needle. The or each spring preferably extends respectively between the first and second parts; the first and third parts; or second and third parts. The cover may be mounted on, or integral with, the spring.

The assembly may be arranged to only permit the needle to extend from the housing if the second part is moved to a required orientation substantially before the second part is moved significantly towards the first part. At least an inner part of the restrictive part of the housing may be provided with indents in the inner cross-section thereof such that the end of the needle will tend to catch in a one of the indents if not fully in the required orientation when the second part is moved towards the first part, to prevent further rotation towards the required orientation.

The assembly is preferably arranged to be mountable on a needle instrument. The assembly is preferably releasably mountable on a needle instrument, and mounting means may be provided on the first part.

The invention further provides a needle instrument incorporating a needle assembly according to any of the preceding thirty one paragraphs.

The invention also provides a syringe incorporating a needle assembly according to any of said preceding thirty one paragraphs.

Embodiments of the present invention will now be described by way of example only and with reference to the accompanying drawings, in which:

FIG. 7 is a diagrammatic not fully to scale, perspective view of the apparatus of FIG. 6 in the same condition;

FIGS. 8 A–I are cross-sectional views of the apparatus of FIG. 7 at respective locations marked thereon;

Figure 1:
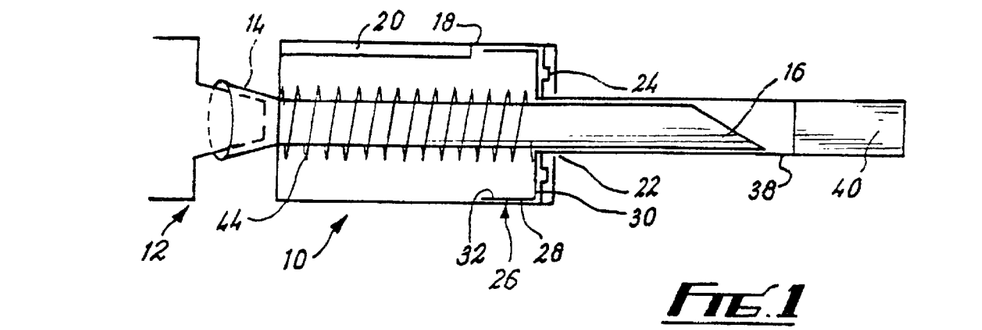
FIG. 1 is a diagrammatic partially cross-sectional side view of a first needle assembly according to the present invention in a first condition.

FIGS. 1 to 5 of the drawings show a first needle assembly 10, which in FIG. 1 is mounted on a conventional syringe 12 only part of which is shown. The assembly 10 comprises a frusto conical needle holder 14 mountable on the syringe 12 and from which a needle 16 extends. The needle 16 has an elliptical cross-section with the longest diameter thereof extending vertically in the drawings. The needle 16 co-axially extends through a cylindrical hollow body 18 which is rigidly mounted on the holder 14. An elongate projection 20 extends internally from the underside of the top of the hollow body 18 as shown in the drawings for approximately two thirds of the length thereof from the end adjacent the needle holder 14. The needle 16 extends through a central hole 22 in the hollow body 18 at the end thereof away from the holder 14. Two square recesses 24 are provided in the end wall of the hollow body 18 above and below the hole 22.

A movable member 26 locates within the hollow body 18 and extends therefrom through the hole 22. The member 26 comprises a first portion 28 which is slidingly movable in the hollow body 18. The portion 28 is hollow and comprises an end face 30 which faces away from the holder 14, and a circumferential side wall 32. An elongate slot 34 is provided on the side wall 32 parallel to the needle 16. The slot 34 is shaped to accept the projection 20 when the first portion 28 is aligned with the hollow body 18, and the first portion 28 is spaced from the hole 22. A pair of square projections 36 are provided on the end face 30 and are locatable within the recesses 24 when the movable member 26 is aligned with the hollow body 18.

Figure 5:
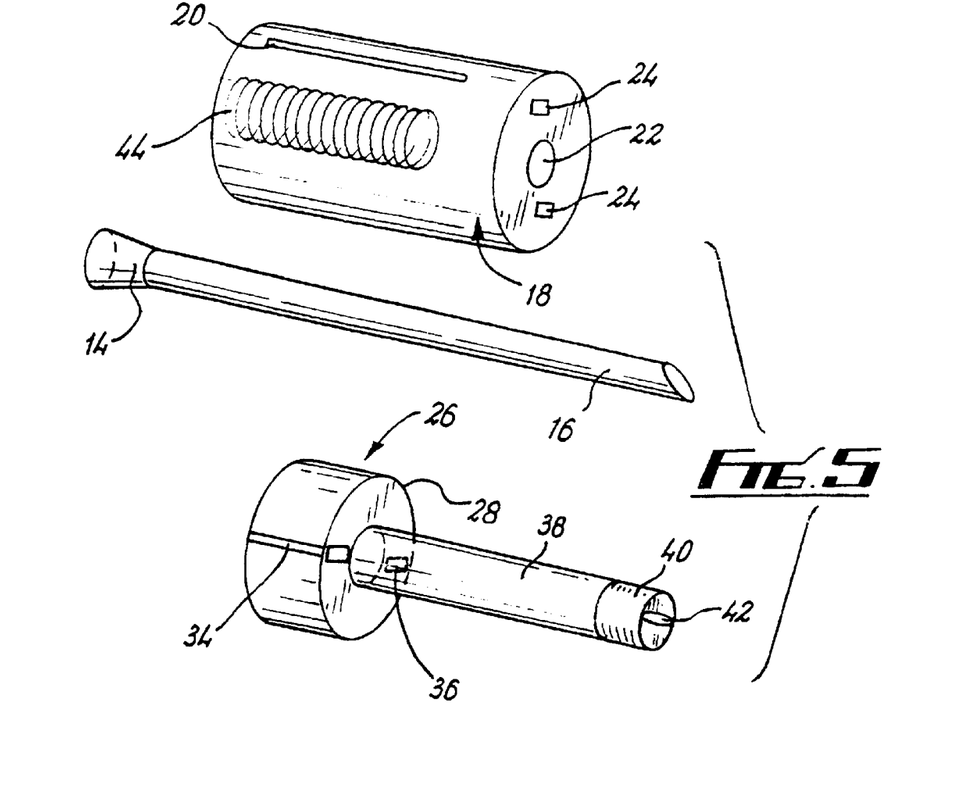
FIG. 5 is a diagrammatic perspective view of the components of the apparatus of FIG. 1.

The movable member 26 further comprises a cylindrical tube 38 which extends from the end face 30 slidingly through the hole 22. A restrictive portion 40 is provided in the free end of the tube 38 and comprises a solid member with an elliptical axial opening 42 extending therethrough. The opening 42 is of a size to allow the needle 16 to slidingly pass therethrough when in a substantially parallel alignment. The portion 40 is sufficiently long to prevent the tip of the needle 16 extending therefrom except when in a parallel alignment. The opening 42 may have a semi-soft surface to prevent blunting of needle due to engagement therewith.

A helical spring 44 extends from the opposite side of the end face 30 of the first portion 28 and is mounted thereto, and also to the end of the hollow body 18 adjacent the holder 14. The spring 44 urges the first portion 28 away from the holder 14 and to an alignment with the largest dimension of the opening 42 substantially horizontal as shown in the drawings.

Figure 2:
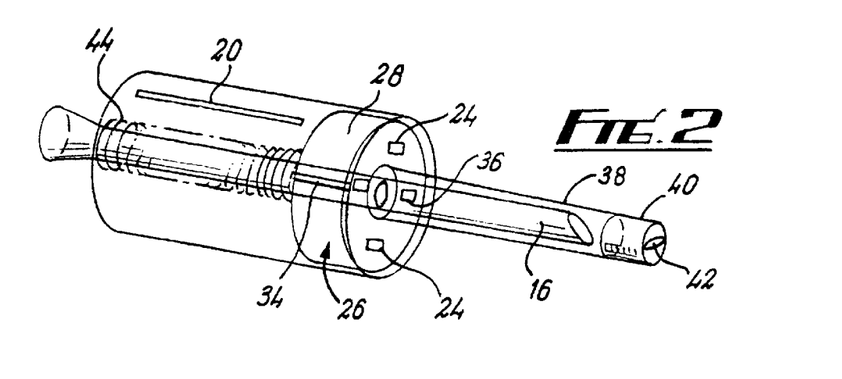
FIG. 2 is a diagrammatic perspective view of the apparatus of FIG. 1 in the same condition.
Figure 4:
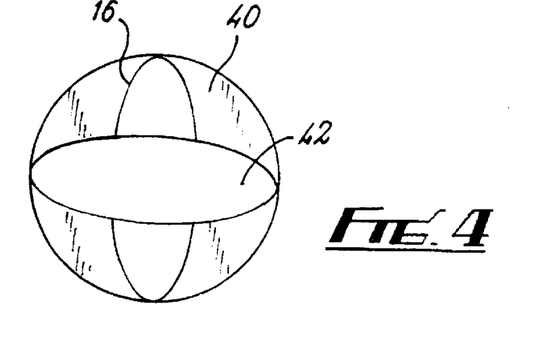
FIG. 4 is a diagrammatic end view of the apparatus of FIG. 1 in the first condition.

In use the assembly 10 will adopt the position shown in FIGS. 1, 2 and 4 in a rest condition. The horizontal alignment of the opening 42 prevents access to the needle 16 even if the first portion 28 is pushed towards the needle holder 14. When it is required to use the assembly 10 to for example inject a substance from the syringe 12 or to collect a sample thereinto, the tube 38 is rotated until the opening 42 is vertically aligned at which point the projections 36 will engage in the recesses 24 by virtue of the urging of the spring 44. The assembly will therefore be held in a position ready for use. The rotation may be provided by holding or fixing the tube 38 and rotating the hollow body 18.

Figure 3:
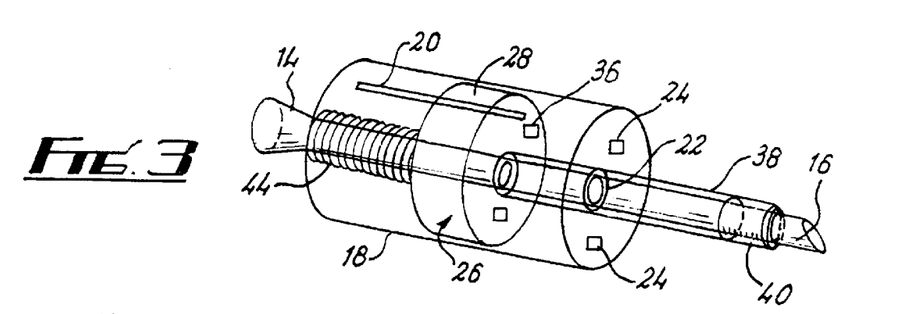
FIG. 3 is a diagrammatic perspective view similar to FIG. 2 but with the apparatus in a second condition.

The assembly 10 can then be pushed against the subject to be injected or from whom a sample is to be taken and the tube 38 and hence first portion 28 will be pushed into the hollow body 18 thereby exposing the needle 16. Initially the tube 38 will be prevented from rotating by virtue of friction against the subject or can be held in position. The end of the tube 38 may be provided with a roughened surface to increase the friction against a subject. Once the needle 16 enters the portion 40 and hence opening 42 and also the projection 20 enters the slot 34, both of these features prevent relative rotation between the hollow body 18 and the first portion 28.

Once the injection or sample taking is complete the needle 16 is withdrawn from the subject. As this withdrawal takes place the tube 38 will move out of the hollow body 18. The needle 16 will eventually pass through the opening 42, and thereafter the first portion 28 will return by virtue of the spring 44 to a position fully away from the holder 14 and with the opening 42 horizontally aligned. At that stage accidental contact with the needle 16 will not be possible.

There is thus described a needle assembly which immediately following injection or sample taking automatically provides for retraction of a protective covering for the needle whereby to prevent accidental injury to a user. The needle will generally only be exposed following a deliberate attempt to provide the required alignment. The assembly would also prevent a person such as a child who finds such a needle from accidentally injuring themselves on it. This assembly is particularly suited for use in highly infectious situations such as AIDS disease. The assembly is of relatively simple configuration and can thus be inexpensively and robustly manufactured.

Whilst the above example is described in relation to a syringe, such an assembly could be provided for a wide range of needle instruments such as drips, vacutainers, butterfly/scalp veins, lumbar puncture needles. When used with a syringe the assembly could be formed to be integral with the remainder of the syringe. Similarly, this arrangement could be modified to fit on to other applications based on the same principle. The needle may be hollow or solid, and in the latter case may be required to puncture the skin or elsewhere. The invention is also applicable to elongate projections other than needles.

Figure 6:
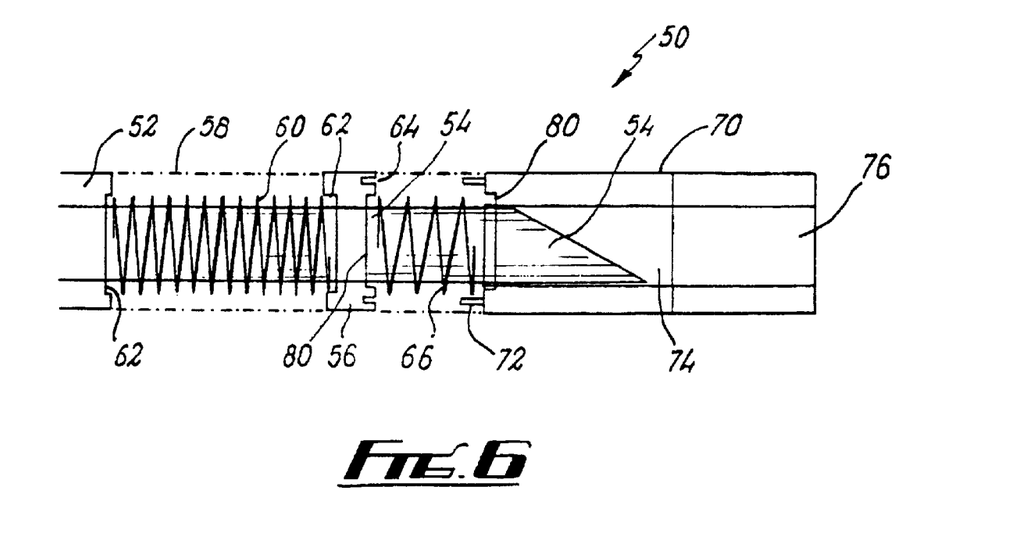
FIG. 6 is a diagrammatic partially cross-sectional view of a second needle assembly according to the present invention in a first condition.
Figures 7, 8A, 8I:
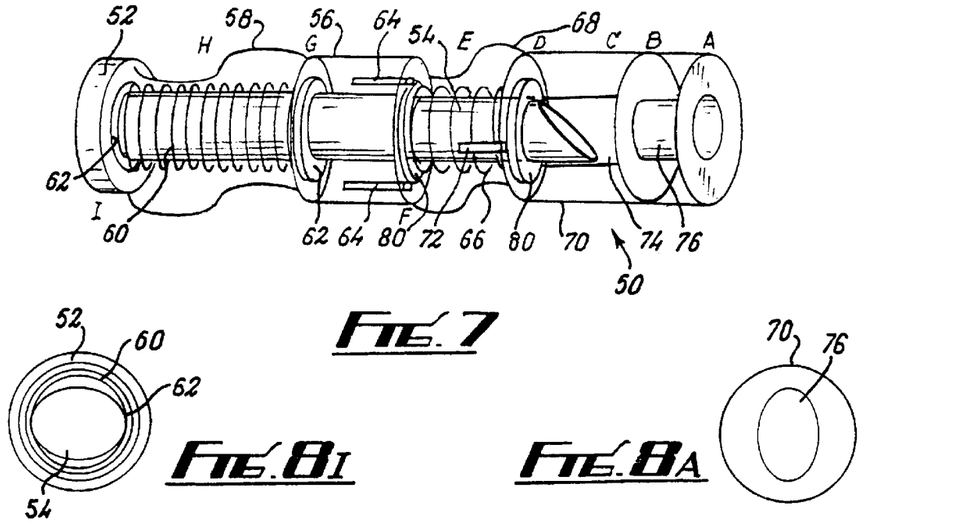
Figures 8B, 8C, 8D, 8F, 8G, 8H:
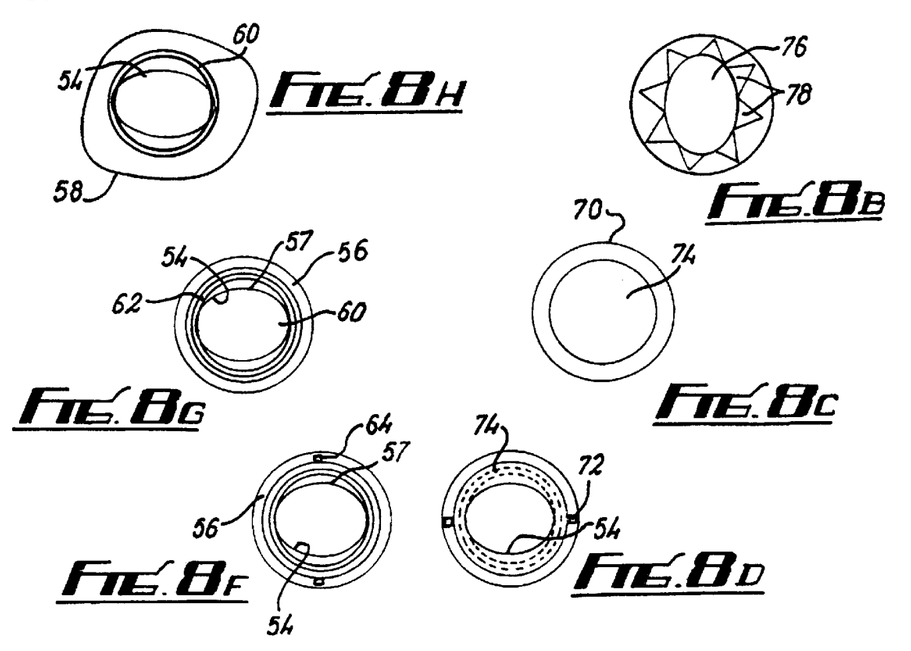
Figure 8E:
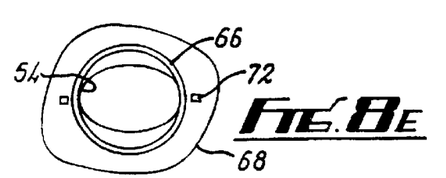

FIGS. 6–8 show a second needle assembly 50 according to the invention. Whilst this assembly can be used in a wide range of applications it is particularly suited for applications such as taking blood where it is required for there to be no contact with the blood, and needles are usually disposed of immediately after use. The assembly 50 could be fitted with a quick release mechanism onto an appropriate self-sealing container, and the assembly discarded immediately after use.

The assembly 50 comprises a first member 52 which is releasably mountable on a required needle instrument (not shown) by any appropriate arrangement. An elliptical cross-section needle 54 extends from the first member 52, which needle 54 is similar to the needle 16. A cylindrical member 56 with a similar elliptical cross-section through passage 57 slidingly and non-rotatably fits on the needle 54 and is connected to the first member 52 by a flexible substantially inelastic sleeve 58 extending around the needle 54. The exterior diameter of the first member 52, sleeve 58 and cylindrical member 56 is substantially equal, as it is for the other components of the assembly.

A spring 60 extends between the first member 52 and the cylindrical member 56 and urges these apart until the sleeve 58 is fully stretched. Annular recesses 62 are provided in each of the first and cylindrical members 52,56 to receive the ends of the spring 60.

Two square section longitudinal recesses 64 are provided in the opposite side of the cylindrical member 56 to the first member 52, and as shown in FIGS. 6 and 7 are diametrically opposite each other one above and one below the needle 54. A further spring 66 and flexible substantially inelastic sleeve 68 extend from the opposite side of the cylindrical member 56 to the first member 52. The spring 66 and sleeve 68 each extend to a second cylindrical member 70. Two diametrically opposed projections 72 are provided on the face of the second cylindrical part 70 which faces towards the first cylindrical member 56. The spring 66 and sleeve 68 are arranged such that in a rest position and as shown in FIGS. 6 and 7, the projections 72 are diametrically on either side of the needle 54, i.e. are equispaced from the two recesses 64.

A passage is provided extending through the second cylindrical member 70. A first part 74 of the passage towards the first cylindrical member 56 is of substantially circular cross-section such as to permit the second cylindrical member 70 to be rotated relative to the needle 54, which in a rest position just extends into the part 74. A second part 76 of the passage is of elliptical cross-section of a size for the needle 54 to slidingly fit therethrough, and only when in a similar alignment. The greatest diameter of the needle 54 is horizontal as shown in the drawings, whilst in a rest condition the greatest diameter of the second member 76 is vertical. The end of the second member 76 of the passage towards the second cylindrical member 56 is provided with a plurality of outwardly extending indents 78, as is shown in FIG. 8B. Similar annular recesses 80 are provided in the facing ends of the first and second cylindrical members 56,70. External markings (not shown) are provided on the first and second and third cylindrical members 52,56 and 70 in line with at least one of the recesses 64 and its corresponding projection 72.

In use, with the assembly 50 fitted on a required needle instrument, the needle 54 can be exposed for use as follows. The second cylindrical member 70 is rotated against the force of the spring so that the marking thereon is aligned with the marking on the first cylindrical member 56, and the first and second cylindrical members 56,70 are moved towards each other such that the respective projections 72 engage in the respective recesses 64 preventing relative rotation between the cylindrical members 56,70, and the distal end of the needle 54 will enter the second part 76 of the passage.

Further movement of the second cylindrical member 70 causes the first cylindrical member 56 to be moved towards the first member 52 against the force of the spring 60 which permits the distal end of the needle 54 to be exposed beyond the second cylindrical member 70 for use. The second cylindrical member 70 can obviously be moved as far towards the first member 52 as is permitted by compression of the springs 60,66.

Once use is complete a user will release the second cylindrical member 70 which will move away from the first member 52 and first cylindrical member 56 by virtue of the urging of the springs 60,66. Once the projections 72 are free of the recesses 64 the spring 66 will cause the second cylindrical member 70 to rotate out of alignment with the needle 54 to prevent accidental access thereto.

The provision of the indents 78 prevents accidental rotation of the second cylindrical member 70 if for instance it is pushed towards the first member 52 inadvertently. The distal end of the needle 54 will catch in a one of the indents 78 thereby preventing further rotation of the second cylindrical part 70 towards alignment with the needle 54.

There is thus described an assembly which can be fitted onto conventional needle instruments whilst providing security against accidental or inadvertent contact with the needle. The sleeves may be mounted on the springs, and may be integral therewith. Rather than recesses being provided on the first cylindrical member and projections on the second, these could be provided the other way round. It may be that only one spring could be required in some instances.

Radial projections, which may not be rigid, may be on the first member and the second cylindrical member, which projections could be gripped together when the needle is fully extended.

Figure 9:
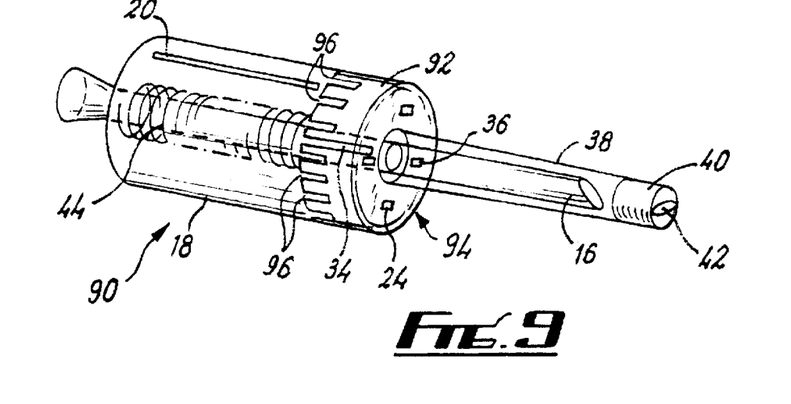
FIGS. 9 and 10 are similar views respectively to FIGS. 2 and 3, of a third needle assembly according to the present invention.
Figure 10:
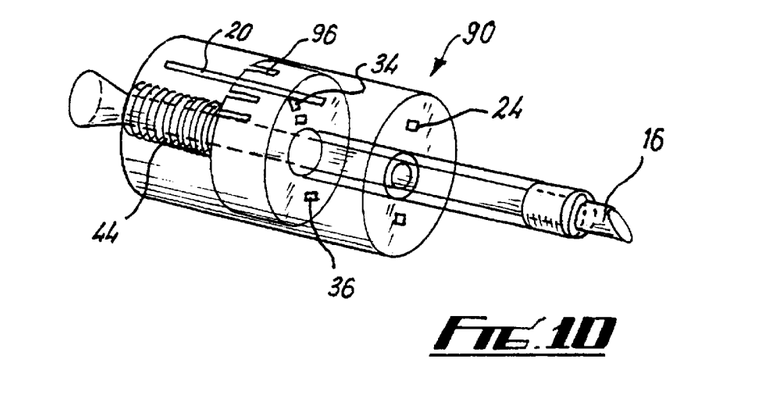

FIGS. 9 and 10 of the drawings show a third needle assembly 90. The assembly 90 is similar to the assembly 10 in most respects, and only the differences will be highlighted. Similar reference numerals have been used for similar components. In the assembly 90, the first portion 92 of the movable member 94 comprises a plurality of blind slots 96 in addition to the elongate slot 34. The assembly 90 comprises a similar initial alignment arrangement, consisting of recesses 24 and projections 36.

Accordingly, the elongate projection 20 can locate in one of the blind slots 96 and permit just limited movement of the movable member 94. The blind slots 96 are of a length such that the projection 20 will reach the closed end thereof before the needle 16 emerges from the free end of the tube 38.

This arrangement provides for extra security and ensures that the needle 16 can only be used when correct alignment of the various components is achieved.

Figure 11:
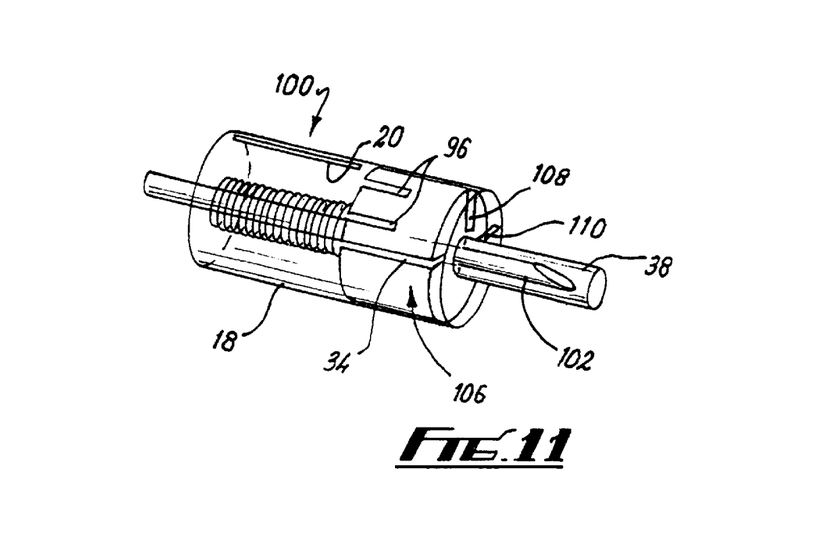
FIG. 11 is a diagrammatic shallower perspective view of a fourth needle assembly according to the present invention in a first condition.

FIG. 11 of the drawings show a fourth needle assembly 100. The assembly 100 is similar in most respects to the assembly 90, and again therefore only the differences will be highlighted. The assembly 100 comprises a circular cross-section needle 102. Again a single slot 34 is provided extending along the first portion 104 of the movable member 106, with a plurality of blind slots 96. A different initial alignment arrangement is provided on the end of the housing member 94. In this instance a single radial projection 108 is provided on the first portion 104, which abuts against a corresponding radial projection 110 on the end wall of the hollow body 18.

In use, the engagement of the projection 20 in the slot 34 is the only way to permit the needle 102 to extend from the tube 38. The blind slots 96 are of such a length that when the projection 20 fully locates in a one thereof, the needle 102 is still wholly within the tube 38. As a circular section needle is used no particular end portion is required. This arrangement permits conventional circular section needles to be used which can be particularly useful when dealing with small diameter needles.

Various other modifications may be made without departing from the scope of the invention. For example, the restrictive portion may be differently shaped. The restrictive portion and/or needle may have a different cross-sectional shape. For instance they may have any non-circular shape such as oval, or polygonal and particularly triangular. The needle could have a closed end and a side opening.

Rather than the projections on the movable member in the first embodiment being engageable in recesses in the hollow body, they may engage against abutments provided inside the hollow body, when the movable member is rotated to the required alignment for the needle to emerge. The projections and abutments preferably have sufficient depth to be engageable until the projection 20 enters the slot 34.

Where more than one retaining means is included, these may be arranged such that as one disengages another one automatically simultaneously engages.

The hollow body may be fenestrated with varying sized diameters to let air escape from the hollow body at varying rates as the assembly returns to an empty condition. This means the movement of the hollow body slows down at the end of this movement to provide sufficient time for the spring to rotate the movable member away from the particular alignment.

It may be possible for only part of the needle to have a non-circular cross-section. In some of the described examples the cylinder is illustrated as being at least translucent such that a visual indication of correct alignment is provided by virtue of the projection 20 and slot 34. If the hollow body is opaque or in addition to the above, a visual indication could be provided on the cylinder and the movable member such as lines or dots to indicate when adjacent each other that the correct alignment of the needle has been achieved. A different arrangement for retaining this correct alignment could be provided. A different spring arrangement could be provided, and rather than a spring a different resilient means may be utilised. The restrictive portion may have other than a flat end, and may have an inclined surface for e.g. collecting blood, or side wings attached to enable easy operability.

The assembly may be arranged to only permit the needle to extend from the hollow body if the second portion is moved to a required orientation substantially before the second portion is moved significantly towards the first part. At least an inner part of the restrictive part of the housing may be provided with indents in the inner cross-section thereof such that the end of the needle will tend to catch in a one of the indents if not fully in the required orientation when the second part is moved towards the first part, to prevent further rotation towards the required orientation.

Whilst endeavouring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

What is claimed is:

1. A needle assembly, the needle assembly comprising a housing and a needle extendable therefrom characterized in that the needle has a non-circular cross-section for at least part of its length, and the housing has a restrictive part with a non-circular cross-section in which the needle is located and from which the needle can selectively extend, the assembly being arranged such that the non-circular needle or part thereof can only extend through the restrictive part and hence from the housing, when in a particular alignment relative to the non-circular cross-section of the restrictive part of the housing.

2. A needle assembly according to claim 1, characterized in that means are included to provide a visual indication when the needle is in the particular relative alignment.

3. A needle assembly according to claim 1, characterized in that the housing comprises a first part rigidly fixed relative to the needle and a second part movable relative to the needle, the second part being movable when the needle is in the particular alignment to a use position wherein the needle extends from the housing.

4. A needle assembly according to claim 3, characterized in that the first part is in the form of a receptacle which movably locates a portion of the second part and from which a further portion of the second part extends, with a greater portion of the second part being located in the first part when in the use position.

5. A needle assembly according to claim 3, characterized in that the needle extends through the first part.

6. A needle assembly according to claim 3, characterized in that the second part includes the restrictive part.

7. A needle assembly according to claim 3, characterized in that a component of the second part is slidably movable within the first part.

8. A needle assembly according to claim 3, characterized in that the second part comprises a circular cross-section tubular part in which the distal end of the needle is slidingly and rotatably located in a non-use condition, with the restrictive part being provided at the distal end of the tubular part.

9. A needle assembly according to claim 3, characterized in that the second part is spring urged away from the use position and/or the particular relative alignment with the needle.

10. A needle assembly according to claim 3, characterized in that first means are provided for selectively retaining the needle and second part in said particular alignment when the needle is located wholly within the housing.

11. A needle assembly according to claim 10, characterized in that second means are provided for selectively retaining the needle and second part in said particular alignment when the needle extends from the housing.

12. A needle assembly according to claim 7, characterized in that guide means are provided which only permit the second part to move into the first part when in said particular alignment.

13. A needle assembly according to claim 3, characterized in that the first part comprises a cylinder.

14. A needle assembly according to claim 1, characterized in that both the restrictive part and the needle are substantially oval or elliptical, with the needle only slidingly fitting through the restrictive part when in a substantially parallel alignment thereto.

15. A needle assembly according to claim 7, characterized in that the second part between said component and the restrictive part comprises a tube through which the needle is movable.

16. A needle assembly according to claim 3, characterized in that the housing between the first and second parts comprises a variable length portion such that the housing can reduce in length to permit the needle to extend therefrom.

17. A needle assembly according to claim 16, characterized in that the housing comprises a third part located between the first and second parts, which third part has a non-circular through passage through which the needle is slidably but substantially not rotatably extendable.

18. A needle assembly according to claim 3, characterized in that the assembly is arranged to only permit the needle to extend from the housing if the second part is moved to a required orientation substantially before the second part is moved significantly towards the first part.

19. A syringe incorporating a needle assembly according to claim 1.

* * * * *

UNITED STATES PATENT AND TRADEMARK OFFICE
CERTIFICATE OF CORRECTION

PATENT NO. : 6,689,107 B1
DATED : February 10, 2004
INVENTOR(S) : Prajendra Pandurang Choudhary It is certified that error appears in the above-identified patent and that said Letters Patent is hereby corrected as shown below:

<u>Title page,</u>
Item [76], Inventors, "Prajenda" should be deleted and replaced with -- Prajendra --.

Signed and Sealed this

Twenty-second Day of June, 2004

JON W. DUDAS
*Acting Director of the United States Patent and Trademark Office*